United States Patent [19]
Willert et al.

[11] Patent Number: 5,171,323
[45] Date of Patent: Dec. 15, 1992

[54] FEMORAL HEAD PROSTHESIS

[75] Inventors: Hans-Georg Willert, Gottingen, Fed. Rep. of Germany; Rudolf Koch, Berlingen, Switzerland

[73] Assignee: Sulzer Brothers Limited, Winterthur, Switzerland

[21] Appl. No.: 673,018

[22] Filed: Mar. 21, 1991

[30] Foreign Application Priority Data

Apr. 10, 1990 [CH] Switzerland ............. 01212/90

[51] Int. Cl.⁵ ............................................. A61F 2/36
[52] U.S. Cl. ................................. 623/23; 623/18; 623/20
[58] Field of Search ............... 623/16, 18, 23, 22

[56] References Cited

U.S. PATENT DOCUMENTS

| 4,938,774 | 7/1990 | Tepic | 623/23 |
| 5,041,140 | 8/1991 | Teinturier | 623/23 |

FOREIGN PATENT DOCUMENTS

| 0308297 | 3/1989 | European Pat. Off. | |
| 0354142 | 2/1990 | European Pat. Off. | |
| 2425237 | 12/1979 | France | |
| 2483218 | 5/1980 | France | 623/22 |
| 2549717 | 2/1985 | France | |
| 2639822 | 12/1988 | France | 623/22 |
| 89/01321 | 2/1989 | World Int. Prop. O. | |

Primary Examiner—David J. Isabella
Assistant Examiner—G. Gualtieri
Attorney, Agent, or Firm—Kenyon & Kenyon

[57] ABSTRACT

A femoral head prosthesis is provided with a slot which extends from ventral to dorsal within the distal zone of the stem to separate a tongue-like core from a resilient peripheral portion. The tongue-like core is able to move in the slot in response to bending and twisting stresses. The shear forces which these stresses produce in a transition zone between the bone and the stem are thus, at least, reduced. The slot may be of U-shape with arms parallel to the sides of the stem or with arms parallel to the axis of the stem. One arm of the slot may also be shorter than the other and one arm may be of widening shape relative to the other.

7 Claims, 2 Drawing Sheets

FEMORAL HEAD PROSTHESIS

This invention relates to a femoral head prosthesis.

Heretofore, various types of femoral head prostheses have been known for implantation in a femur bone. In some cases, the femoral head prosthesis has been provided with a fixing stem which widens conically on all sides from a distal zone to a promixal zone and which is formed with at least one substantially longitudinal narrow slot extending through the thickness of the stem, for example, from ventral to dorsal. Such a prosthesis is described in French Patent 2 549 717. In such cases, the narrow longitudinal slot is intended to enhance the resilience of the mainly metal stem so that during implantation in a bone, the slot serves to prevent excessive pressure peaks and, thus, reduces the risk of the bone shattering. Also, as a result of high resilience of wide zones, the slot is to enable the stem to adapt to curvatures and unevenness in the femur cavity and thus insure engagement with the bone over a relatively large area.

However, as is conventional in previous stem constructions, in this known prosthesis, the forces produced by bending of the spherical head of a femur, particularly alternating shear and twisting forces in the distal zone in response to stresses being applied to and removed from the stem, must be transmitted through or taken up by the "boundary surface" between the bone and the prosthesis.

Other types of prostheses which have been provided with slots in the stem have also been known from European Patent Application 0 308 297 and International Application WO89/01321.

It has also been known from European Patent Application 0 354 142 to provide slots in a proximal zone of a femoral prosthesis to enhance implantation. Still further, it has been known from French Patent 2 425 237 to form a femoral prosthesis of multiple parallel rod elements to enhance resilience.

It is an object of the invention to provide a femoral head prosthesis in which the resilience of the stem in a distal zone can be approximated to that of a bone with the transition zone from the prosthesis to the bone or a bone cement bed relieved at least to a considerable extent of shear and twisting forces.

It is another object of the invention to enhance the resilience of a fixing stem of a femoral head prosthesis.

It is another object of the invention to provide a fixing stem for a femoral head prosthesis which is resilient and which is able to take up alternating shear and twisting forces in a distal zone.

Briefly, the invention provides a femoral head prosthesis having a fixing stem of conically widening shape from a distal end towards a proximal end with a slot of U-shape which extends therethrough within a distal zone from ventral to dorsal in order to separate a tongue-like core from a resilient peripheral portion.

Due to the shape of the slot, the tongue-like core of the fixing stem can yield considerably to forces caused by bending moments applied to a femoral head without substantial shear and torsion stresses arising in a transition zone between the prosthesis and a bone.

The tongue-like core of the fixing stem is able to move relative to the resilient peripheral portion of the stem both medially to laterally as well as from ventral to dorsal. In addition, the tongue-like core may undergo twisting movements around a longitudinal axis thereof.

If the resilient peripheral portion is required to have a substantially constant bending stress over the whole height of the slot, the longitudinal arms of the slot extend, conveniently, parallel to the stem axis. Alternatively, the arms of the slot may extend parallel to the external sides of the stem so that the bending stress in the peripheral portion of the stem increases proximally.

The stem may have different rigidities medially and laterally of the central axis if the slot arm which extends laterally of the stem axis is shorter than the medial arm. This feature obviates an excessive lateral deflection of the core which is otherwise likely to make the core contact the lateral arm of the resilient peripheral portion. Any such contact should, as far as possible, be avoided, as otherwise, the relative movements produce unwanted metal abrasion.

In order to enable the core to deflect laterally to a considerable extent, the lateral arm of the slot may be of conical shape of increasing width in the distal direction while being wider than the medial arm of the slot.

These and other objects and advantages of the invention will become more apparent from the following detailed description taken in conjunction with the accompanying drawings wherein.

Figure 1:
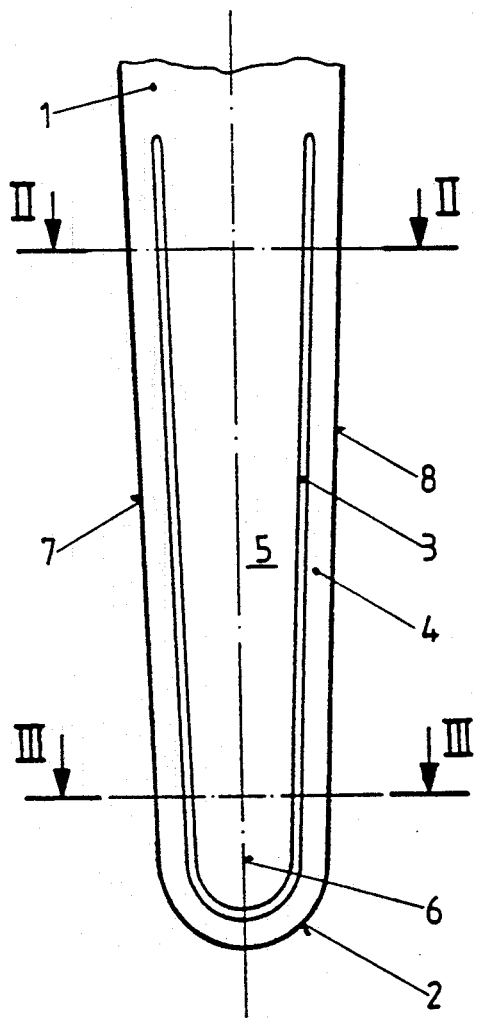
FIG. 1 illustrates a ventral side view of a distal end of a femoral head prosthesis constructed in accordance with the invention.

Referring to FIG. 1, the femoral head prosthsis has a fixing stem 1 of conically widening shape from a distal end towards a proximal end. In this respect, only the distal zone of the stem is illustrated. In addition, the stem 1 is provided with a slot 3 which extends therethrough within the distal zone from ventral to dorsal in order to separate a resilient peripheral portion 4 from a central tongue-like core 5. The resilient peripheral portion 4 (edge zone) is able to engage a bone or cement bed (not shown).

The slot 3 is of a width of from 0.5 to 1 millimeters and has a pair of arms conically disposed relative to a central axis 6 of the stem and parallel to the respective external sides 7, 8 of the stem 1.

Figure 2:
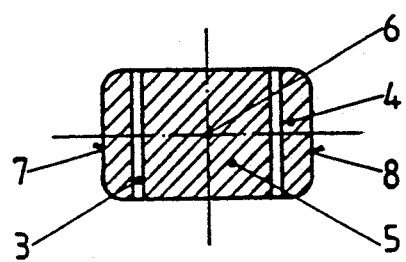
FIG. 2 illustrates a cross-sectional view taken on line II—II of FIG. 1.
Figure 3:
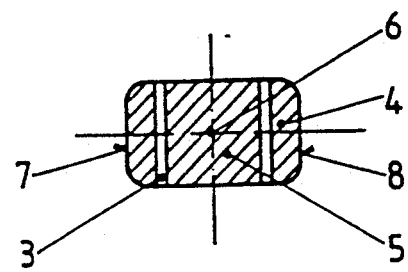
FIG. 3 illustrates a cross-sectional view taken on line III—III of FIG. 1.

After implantion in a bone, when a femoral head (not shown) is subjected to bending stresses, the core 5 may move into the slot 3 both laterally to medially, i.e., horizontally in the plane of FIGS. 2 and 3 as well as ventrally to dorsally, i.e., vertically in the plane of FIGS. 2 and 3. The core 5 may also rotate about the longitudinal axis 6.

The width of the slot 3 must meet two conflicting requirements. First, the slot 3 must be narrow enough to prevent any invasion of bone tissue. Hence, the width of the slot 3 is limited to approximately one milimeter. Second, the slot 3 should be wide enough for the tongue-like core 5 not to completely bridge the slot 3 and contact the peripheral edge portion 4 during the movements described because if the core 5 and peripheral portion 4 contact one another there will be an unwanted abrasion of metal.

Figure 4:
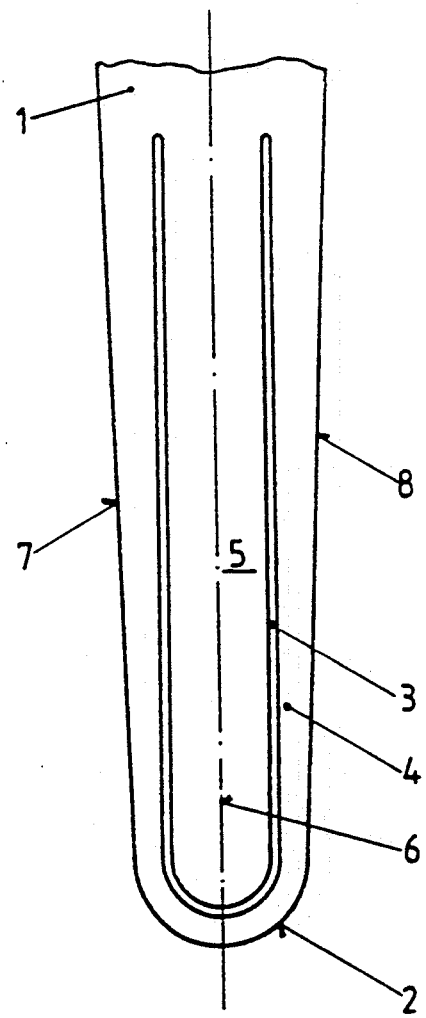
FIG. 4 illustrates a view of a modified prosthesis having a U-shaped slot with parallel arms in accordance with the invention.

Referring to FIG. 4, wherein like reference characters indicate like parts as above, the slot 3 may be of U-shape with a pair of arms extending parallel to each other and to the central axis 6. In this case, the core 5 has a rigidity or resilience which is constant over the whole height of the slot 3. In the embodiment of FIG. 1, the core 5 has a rigidity or resilience which increases proximally due to the increasing thickness of the core 5.

Figure 5:
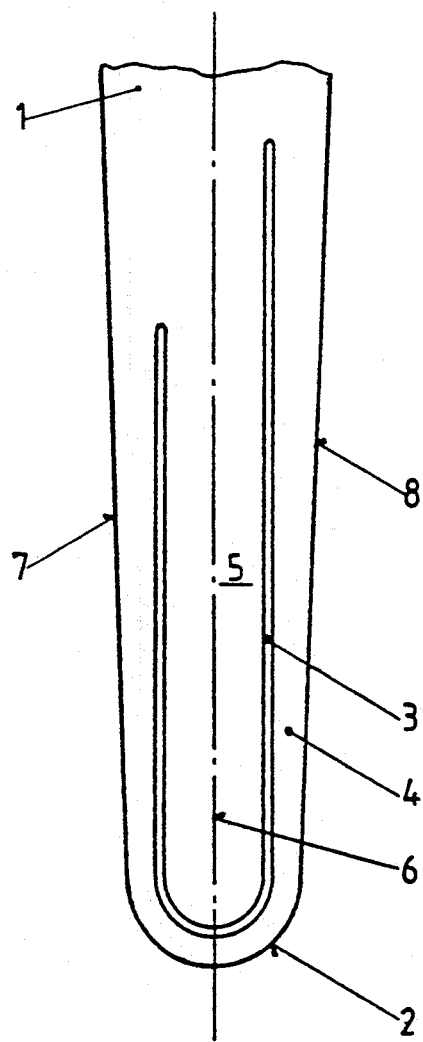
FIG. 5 illustrates a futher modified stem having a U-shaped slot with arms of different length.

Referring to FIG. 5, wherein like reference characters indicate like parts as above, the slot 3 may be of U-shape with the lateral arm being of shorter length than the medial arm. This provides different core rigidities laterally and medially of the longitudinal axis 6.

Figure 6:
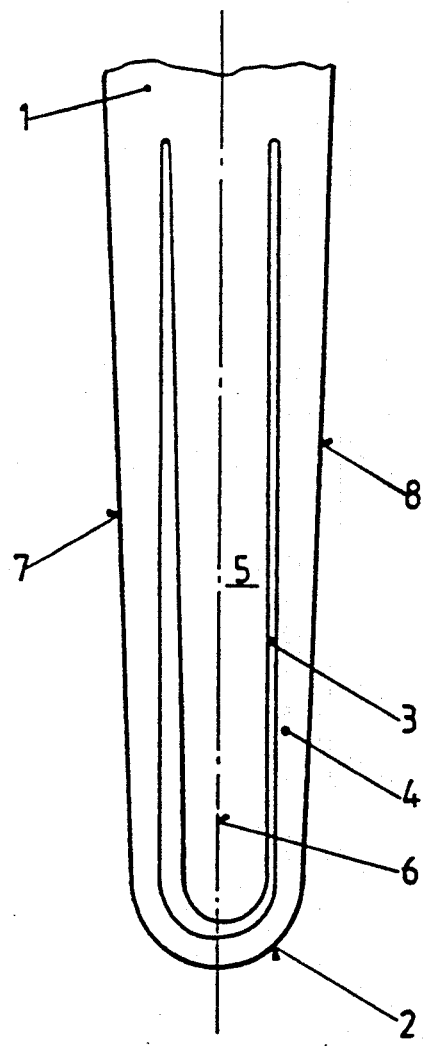
FIG. 6 illustrates a view of a stem having a slot width one arm being of conical shape and of increasing width in a distal direction according to the invention.

Referring to FIG. 6, wherein like reference characters indicate like parts as above, the slot 3 may have a pair of arms with the lateral arm being of conical shape of increasing width in a distal direction while the medial arm is of contant width. As indicated, both arms are of the same width at the proximal end of each. By way of example, the widest portion of the lateral arm may have a width of approximately four milimeters at the distal end. In this embodiment, the core 5 has greater provision for movement laterally than medially since the bending stresses in the lateral direction produce greater movement amplitude than in the medial direction. There is no risk of invasion of bone tissue in the widened arm of the slot 3 since the movements which are occurring virtually the whole time after implantation prevent any formation of such bone tissue.

The stem may be made of any suitable implant materials, such as metals and metal alloys, with titanium or a titanium alloy being preferred.

The slot 3 may be formed in the fixing stem by means of a high pressure liquid jet cutting process.

The invention thus provides a fixing stem for a femur prothesis which has an enhanced resilience while at the same time allowing the transfer of bending stresses between a bone and the prosthesis.

A suitable resilience is achieved when the arms of the slot 3 exceed one third of the axial anchoring length of the stem.

What is claimed is:

1. A femoral head prosthesis having a fixing stem of conically widening shape from a distal end towards a proximal thereof portion, said stem including a slot extending continuously therethrough within a distal zone from ventral to dorsal wherein said slot includes two portions, each of said portions extending from a proximal end toward the distal end of the fixing stem, said proximal ends of said portions being separated laterally, and wherein the two portions meet at a point which is separated by a predetermined distance in a substantially distal direction from said proximal ends thereby separating a tongue-like core from a resilient peripheral portion.

2. A prosthesis as set forth in claim 1 wherein said slot is of U-shape with a pair of arms extending parallel to each other.

3. A prosthesis as set forth in claim 1 wherein said slot has a pair of arms, each arm being disposed in parallel to an external side of said stem.

4. A prosthesis as set forth in claim 1 wherein said slot has a pair of arms with one of said arms being of shorter length than the other of said arms.

5. A prosthesis as set forth in claim 1 wherein said slot has a pair of arms, with one of said arms being of increasing width in a distal direction.

6. A prosthesis as set forth in claim 1 wherein said slot has a width of 1 millimeter.

7. A prosthesis as set forth in claim 1 wherein said slot has a pair of arms, at least one of said pair of arms having a length of more than one-third of an axial anchoring length of the stem.

* * * * *

UNITED STATES PATENT AND TRADEMARK OFFICE
CERTIFICATE OF CORRECTION

PATENT NO. : 5,171,323

DATED : December 15, 1992

INVENTOR(S) : Willert et al.

It is certified that error appears in the above-indentified patent and that said Letters Patent is hereby corrected as shown below:

Column 2, line 37, change "width" to --with--;
          line 40, change "prosthsis" to --prosthesis--.

Column 3, line 38, change "prothesis" to --prosthesis--.

Column 4, line 9, change "proximal thereof portion" to --proximal portion thereof--.

Signed and Sealed this

Fourteenth Day of June, 1994

Attest:

BRUCE LEHMAN

*Attesting Officer*     *Commissioner of Patents and Trademarks*